United States Patent
Iacono et al.

(10) Patent No.: US 10,975,032 B1
(45) Date of Patent: Apr. 13, 2021

(54) PERFLUOROPYRIDINE DERIVED AROMATIC MONOMERS AND PROCESSES OF MAKING AND USING SAME

(71) Applicant: Government of the United States, as represented by the Secretary of the Air Force, Wright-Patterson AFB, OH (US)

(72) Inventors: Scott T. Iacono, Colorado Springs, CO (US); Matthew B Houck, Colorado Springs, CO (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 0 days.

(21) Appl. No.: 16/940,430

(22) Filed: Jul. 28, 2020

(51) Int. Cl.
*C07D 213/61* (2006.01)
*C08G 77/04* (2006.01)
*C08G 73/06* (2006.01)

(52) U.S. Cl.
CPC ....... *C07D 213/61* (2013.01); *C08G 73/0627* (2013.01); *C08G 77/045* (2013.01)

(58) Field of Classification Search
None
See application file for complete search history.

(56) References Cited

PUBLICATIONS

Houck et al, ACS Macro Letters, vol. 9, pp. 964-968, Jun. 16, 2020.*
High Temple 2020, Preliminary Agenda, Session 2: High Temperature Resins & Composites, Nov. 15, 2019.*
Corley, C. A.; Kobra, K.; Peloquin, A. J.; Salmon, K.; Gumireddy, L.; Knoerzer, T. A.; McMillen, C. D.; William T. Pennington, W. T.; Schoffstall, A. M.; Scott T. Iacono S. T.; Utilizing the Regioselectivity of Perfluoropyridine towards the Preparation of Phenyoxyacetylene Precursors for Partially Fluorinated Polymers of Diverse Architecture Journal of Fluorine Chemistry, 2019, 1-28.
Houck, M. B.; Brown, L. C.; Lambeth, R. H.; Iacono, S. T.; Exploiting the Site Selectivity of Perfluoropyridine for Facile Access to Densified Polyarylene Networks for Carbon-Rich Materials ACS Macro Lett. 2020, 9, 964-968.
Rondeau-Gagne, S.; Morin, J.; Preparation of carbon nanomaterials from molecular precursors Chem Soc Rev, 2013, DOI: 10.1039/c3cs60210a.
Scott T. Iacono, S. T.; Perpall, M. W.; Wapner, P. G.; Hoffman, W. P.; Smith Jr., D. W.; Carbonization and thermal expansion of glassy carbon derived from bis-ortho-diynylarenes Carbon 2007, 45, 931-935.
Fuhrer, T. J.; Houck, M.; Cynthia A. Corley, C. A.; Iacono, S. T.; Theoretical Explanation of Reaction Site Selectivity in the Addition of a Phenoxy Group to Perfluoropyridine J. Phys. Chem. A XXXX, XXX, XXX-XXX, 2019, DOI: 10.1021/acs.jpca.9b06413.
Houck, M. B.; Perfluoropyridine Based Monomers for Polyaromatic Thermosetting Resins 2020, 1-18.
Liu, C.; Zhao, H.; Zhao, H.; Z. Wang, Z.; Zhang, B.; RSC Adv., 2015, DOI: 10.1039/C5RA04279H.
Houck, M. B.; Corley, C. A.; Iacono, S. T.; Benzocyclobutene (BCB) Derived Perfluoropyridine Monomers for Polyaromatic Thermosetting Resins, Abstract Presented Feb. 4, 2020 at High Temple WorkShop.

* cited by examiner

*Primary Examiner* — Zinna Northington Davis
(74) *Attorney, Agent, or Firm* — AFMCLO/JAZ; James F. McBride

(57) ABSTRACT

The present invention relates to perfluoropyridine derived aromatic monomers and processes of making and using same. Such monomers can be easily and selectively functionalized and yet still synthesized by an efficient and environmentally friendly pathway. In addition, such monomers can be used to produce polymers with highly satisfactory char yields.

22 Claims, No Drawings

PERFLUOROPYRIDINE DERIVED AROMATIC MONOMERS AND PROCESSES OF MAKING AND USING SAME

RIGHTS OF THE GOVERNMENT

The invention described herein may be manufactured and used by or for the Government of the United States for all governmental purposes without the payment of any royalty.

FIELD OF THE INVENTION

The present invention relates to perfluoropyridine derived aromatic monomers and processes of making and using same.

BACKGROUND OF THE INVENTION

Cyanate ester resins are used extensively in a number of applications including the aerospace industry. Unfortunately, the manufacture of such resins requires the use of a number of toxic raw materials and the yields of such manufacturing processes are not ideal. Furthermore, such cyanate esters have a short shelf life, must be used in a carefully controlled manner as they can generate hydrogen cyanide when they undergo hydrolysis and many times they do not cure as evenly as desired and/or give as high a char yield as desired. Attempts have been made to overcome the difficulties associated with cyanate ester resins. However, such attempts yielded systems such as expoy resins which are subject to the many of the same short comings as cyanate esters. As a result of such problems, research focused on bis-ortho-diynylarenes. While have satisfactory char yields the synthesis of such materials requires transition metal chemistry and the ability to functionalize such materials is extremely limited Applicants recognized that the source of the aforementioned problems of bis-ortho-diynylarenes was that of bis-ortho-diynylarenes require two adjacent alkenes in order to be capable of curing and the lack in the variety of precursors of bis-ortho-diynylarenes limits the ability to functionalize bis-ortho-diynylarenes. As a result, of such recognition Applicants worked to discover materials that could be easily and selectively functionalized and yet still synthesized by an efficient and environmentally friendly pathway. As a result of such work, applicants disclose perfluoropyridine derived aromatic monomers and processes of making and using same. Such monomers can be easily and selectively functionalized and yet still synthesized by an efficient and environmentally friendly pathway. In addition, such monomers can be used to produce polymers with highly satisfactory char yields.

SUMMARY OF THE INVENTION

The present invention relates to perfluoropyridine derived aromatic monomers and processes of making and using same. Such monomers can be easily and selectively functionalized and yet still synthesized by an efficient and environmentally friendly pathway. In addition, such monomers can be used to produce polymers with highly satisfactory char yields.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims. For purposes of this specification, headings are not considered paragraphs and thus this paragraph is Paragraph 0006 of the present specification. The individual number of each paragraph above and below this paragraph can be determined by reference to this paragraph's number.

DETAILED DESCRIPTION OF THE INVENTION

Definitions

Unless specifically stated otherwise, as used herein, the terms "a", "an" and "the" mean "at least one".

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Perfluoropyridine Derived Aromatic Monomers, Polymers Comprising Perfluoropyridine Derived Aromatic Monomers and Articles Comprising Same Applicants disclose a monomer having the following formula:

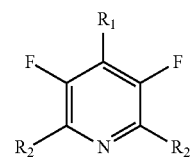

wherein
a) $R_1$ is anthracene or diphenylacetylene.
b) each $R_2$ diphenylacetylene.

Applicants disclose a polymer network comprising the monomer according to Paragraph 0012.

Applicants disclose a polymer network according to Paragraph 0013, said polymer network being a homopolymer network, preferably said homopolymer network has a char yield of at least 50%, more preferably said homopolymer network has a char yield of 50% to about 85% or a char yield of 50% to about 80%.

Applicants disclose an article comprising the polymer network according to Paragraphs 0013 through 0014, said article being a protective high temperature coating and/or sealant for aerospace vehicles, a protective high temperature coating and/or sealant for motor vehicles, and/or a protective insulating coating for electrical systems and wiring.

Applicants disclose an article comprising the polymer network according to Paragraphs 0013 through 0014, said article being said article being an aerospace vehicle, a motor vehicle or an injection molded and/or 3D printed consumer good.

Process of Making Perfluoropyridine Derived Aromatic Monomers and Polymer Networks Comprising Same Applicants disclose a process of making the monomer of Paragraph 0012, said process comprising:
  a) lithiating in a solvent, at a temperature of minus 20° C. to minus 100° C., preferably lithiating at a temperature of minus 40° C. to minus 78° C., more preferably lithiating at a temperature of minus 60° C. to minus 78° C., diphenylacetylene to form lithiated diphenylacetylene; preferably said solvent is diethylether;
  b) maintaining the lithation temperature of said lithiated diphenylacetylene and combining said lithiated diphenylacetylene with perfluoropyridine to form a lithiated diphenylacetylene and perfluoropyridine mixture;
  c) allowing said mixture of lithiated diphenylacetylene and perfluoropyridine to react for about one hour to about three hours, preferably said mixture of lithiated diphenylacetylene and perfluoropyridine is allowed to react for about two hours to about two and one half hours, said mixture of lithiated diphenylacetylene and perfluoropyridine forming a triacetylic monomer and optional impurities;
  c) quenching said reaction, preferably said reaction is quenched by the addition of methanol to said triacetylic monomer and optional impurities, preferably said quenching results in a pH neutral triacetylic monomer;
  d) scavenging unreacted reactants and/or said optional impurities from said triacetylic monomer by forming a mixture that comprises an organic layer and a aqueous layer, said organic layer comprising the triacetylic monomer and said aqueous layer comprising said unreacted reactants and/or optional impurities, preferably said scavenging is by the addition of any aqueous solution of ammonium chloride to said triacetylic monomer;
  e) removing said aqueous layer from said mixture that comprises an organic layer and an aqueous layer, preferably said removing comprises removal using a separatory funnel;
  f) removing moisture from said organic layer, preferably said removal of said moisture comprises adding magnesium sulfate to said organic layer;
  g) filtering off said magnesium sulfate from said organic layer;
  h) removing said solvent from said organic layer, preferably said solvent is removed under reduced pressure, more preferably said solvent is removed via vacuum distillation.

Applicants disclose a process of making the monomer of Paragraph 0012, said process comprising:
  a) lithiating in a solvent, at a temperature of minus 20° C. to minus 100° C., preferably lithiating at a temperature of minus 40° C. to minus 78° C., more preferably lithiating at a temperature of minus 60° C. to minus 78° C., diphenylacetylene; preferably said solvent is diethylether;
  b) maintaining the lithation temperature of said lithiated diphenylacetylene and combining said lithiated diphenylacetylene with perfluoropyridine to form a lithiated diphenylacetylene and perfluoropyridine mixture;
  c) allowing said mixture of lithiated diphenylacetylene and perfluoropyridine to react for about one hour to about three hours, preferably said mixture of lithiated diphenylacetylene and perfluoropyridine is allowed to react for about two hours to about two and one half hours, said mixture of lithiated diphenylacetylene and perfluoropyridine forming a triacetylic monomer and optional impurities;
  c) quenching said reaction, preferably said reaction is quenched by the addition of methanol to said triacetylic monomer and optional impurities, preferably said quenching results in a pH neutral triacetylic monomer;
  d) scavenging unreacted reactants and/or said optional impurities from said triacetylic monomer by forming a mixture that comprises an organic layer and a aqueous layer, said organic layer comprising the triacetylic monomer and said aqueous layer comprising said unreacted reactants and/or optional impurities, preferably said scavenging is by the addition of any aqueous solution of ammonium chloride to said triacetylic monomer;
  e) removing said aqueous layer from said mixture that comprises an organic layer and an aqueous layer, preferably said removing comprises removal using a separatory funnel;
  f) removing moisture from said organic layer, preferably said removal of said moisture comprises adding magnesium sulfate to said organic layer;
  g) filtering off said magnesium sulfate from said organic layer;
  h) removing said solvent from said organic layer, preferably said solvent is removed under reduced pressure, more preferably said solvent is removed via via vacuum distillation.

Applicants disclose a process of making the polymer network of Paragraphs 0013 through 0014 said process comprising the steps of curing the monomer of Paragraph 0012 at a temperature range of 300° C. to 450° C. under a nitrogen atmosphere at a heating rate of 5° C./min.

Applicants disclose the process of Paragraph 0019 comprising combining the monomer of claim 1 with one or more monomers to form a monomer mixture curing said monomer mixture at a temperature range of 300° C. to 450° C. under a nitrogen atmosphere at a heating rate of 5° C./min, preferably said one or monomers is selected from the group consisting of trialkynyl cyanurates, trialkynyl isocyanurates, benzocyclobutanes, bis-ortho-diynyl arenes (BODA), bis-phenylethynyl polyhedral oligomeric silsesquioxanes and mixtures thereof more preferably said one or monomers is selected from the group consisting of trialkynyl isocyanurates benzocyclobutanes, bis-ortho-diynyl arenes (BODA), bis-phenylethynyl polyhedral oligomeric silsesquioxanes and mixtures thereof more preferably said one or monomers is selected from the group consisting of benzocyclobutanes, bis-ortho-diynyl arenes (BODA), bis-phenylethynyl polyhedral oligomeric silsesquioxanes and mixtures thereof; more preferably said one or monomers is selected from the group consisting of bis-ortho-diynyl arenes (BODA), bis-phenylethynyl polyhedral oligomeric silsesquioxanes and mixtures thereof most preferably said one or monomers is selected form the group consisting of bis-phenylethynyl polyhedral oligomeric silsesquioxanes and mixtures thereof.

Materials that are needed to produce the monomers disclosed and/or claimed by Applicants in this specification can be purchased from companies such as: SynQuest Laboratories SynQuest Laboratories, Inc. Alachua, Fla. 32616-0309 USA; Oakwood Chemical 730 Columbia Hwy. N, Estill, S.C. 29918; TCI America 9211 North Harborgate Street Portland, Oreg. 97203 U.S.A.

Aerospace vehicles include those provided in Table 1 below.

TABLE 1

Aerospace Vehicle Type and Modes of Guidance, Navigation, and Control

| Vehicle | GNC Methods | Maneuver Method |
|---|---|---|
| AIR | | |
| Weather Balloon | radiosonde, theodolite | pressure inside balloon |
| Manned aircraft | altimeter, inertial navigation system (INS), Global Positioning System (GPS) | thrust, flight control surfaces |
| Unmanned aircraft | altimeter, INS, GPS | thrust, flight control surfaces |
| Quadcopter | visual sensor, GPS | propeller(s) |
| Airborne Missile | altimeter, INS, GPS | thrust, flight control surfaces |
| AEROSPACE | | |
| Scientific Balloon | star camera, altimeter | pressure inside balloon |
| Sounding Rocket | ring laser gyro, altimeter, accelerometers | thrust, flight control surfaces |
| Space Shuttle | human-in-the-loop, star camera | thrust, flight control surfaces |
| Launch Vehicle (Rocket) | INS, ring laser gyro, altimeter, accelerometers | thrust, flight control surfaces |
| Ballistic Missile | INS, GPS | thrust, flight control surfaces |
| SPACE | | |
| Satellite | star camera, sun sensor, horizon sensor, GPS | thruster, electric propulsion, magnetorquer, momentum wheel |
| Space Station | human, star camera, sun sensor, horizon sensor, GPS | thruster, electric propulsion, magnetorquer, momentum wheel |
| Interplanetary Vehicle | star camera, sun sensor | thruster, electric propulsion, momentum wheel |

Examples of Flight Control Surfaces: Fins, Ailerons, Elevators.

Thrust includes the two-directional thrust force, as well as any gimbaled thrust vectoring the vehicle is capable of generating.

Test Method

For purpose of the present specification and claims, percent char is determined as follows:
1.) The monomer to be investigated is cured to form a polymer network at a temperature range of 300° C. to 450° C. under a nitrogen atmosphere at a heating rate of 5° C./min using a TA DSC Q20 utilizing aluminum pans.
2.) A platinum TGA pan is then pre-weighed using a TA TGA Q500.
3.) The Polymer network to be investigated is then transferred to the pre-weighed platinum TGA pan which is then loaded into the TGA sample loader.
4.) The polymer network is then heated to 900° C. at a heating rate of 5° C./min in an argon atmosphere using a TA TGA Q500. The resulting mass loss is directly recorded and plotted by the TA TGA Q500 to give the resulting char yield of the polymer network at 900° C.

EXAMPLES

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1—Synthesis of 2,3,5,6-tetrafluoro-4-(4-(phenylethynyl)phenyl)pyridine (1). Lithiated diphenylacetylene (generated from 1.521 g, 5.915 mmol 1-bromo-4-(phenylethynyl)benzene) in diethyl ether (30 mL, 0.1972 M) at −78° C. was added dropwise Perfluoropyridine (1.008 g, 5.963 mmol) dissolved in diethyl ether (15 mL) at −78° C. over a period of 10 min, during this time liquid N2 was added periodically to maintain the low temperature of the cold bath. Upon initial addition the reaction mixture turned a deep red/purple and the reaction mixture was allowed to warm to room temperature during which time the reaction mixture turned bright yellow. After 2 h, the reaction was quenched by dropwise addition of methanol (1 mL), followed by the addition of saturated, aqueous ammonium chloride. The top ether layer was extracted 3x, dried over magnesium sulfate, and then concentrated under reduced pressure to give a red viscous oil. The crude product was passed through a silica gel flash column using hexanes/ethyl acetate (Rf 0.81, 75:25, v/v) as the eluent. The collected fractions were vacuum dried to give the desired product as a fluffy, white solid (1.469 g, 75%). The synthesis product was analyzed by nuclear magnetic resonance (NMR) spectroscopy, and high-resolution mass spectrometry (HRMS) techniques and found to be the expected product.

Example 2—Synthesis of 3,5-difluoro-2,4,6-tris(4-(phenylethynyl)phenyl)pyridine (1a). Perfluoropyridine (0.3025 g, 1.789 mmol) dissolved in diethyl ether (15 mL) was added dropwise to lithiated diphenylacetylene (generated from 1.380 g, 5.368 mmol of 1-bromo-4-(phenylethynyl)benzene) in diethyl ether (30 mL, 0.1789 M) at −78° C. over a period of 10 min. The reaction mixture was allowed to warm to room temperature and was stirred for 2 h where upon the white slurry was quenched by dropwise addition of methanol (5 mL) followed by the addition of aqueous ammonium chloride. The top ether layer was extracted, dried over magnesium sulfate, and concentrated under reduced pressure to give a red viscous oil. The crude product was passed through a silica plug using hexanes/ethyl acetate (75:25, v/v) as the eluent and upon rotary evaporation afforded the title compound as a light yellow, waxy solid. X-ray quality crystalline solid was obtained by dissolving the crude oil in diethyl ether and layering the solution on top of deionized water. Crystals began to form at the interface of the biphasic mixture within 1 h and after 24 h, the desired product had fully crystallized, yielding large white crystalline shards which were collected by gravity filtration. The synthesis product was analyzed by nuclear magnetic resonance (NMR) spectroscopy, and high-resolution mass spectrometry (HRMS) techniques and found to be the expected product.

Example 3—Synthesis of 3,5-difluoro-2,6-bis(naphthalen-1-yloxy)-4-(4(phenylethynyl)phenyl)-pyridine (1b). Naphthalen-1-ol (0.3140 g, 2.178 mmol) and cesium carbonate (0.7356 g, 2.258 mmol) were added to 2,3,5,6-tetrafluoro-4-(4-(phenylethynyl)phenyl)pyridine (1) (0.3564 g, 1.089 mmol) dissolved in acetonitrile (45 mL). The reaction mixture was heated to reflux at which point the reaction mixture immediately turned a light green color. After 3 h, the reaction mixture was cooled, vacuum filtered to remove the residual cesium salts, dried under reduced pressure to give a dark solid which was triturated repeatedly with methanol to give a white solid as the desired product. The synthesis product was analyzed by nuclear magnetic resonance (NMR) spectroscopy, and high-resolution mass spectrometry (HRMS) techniques and found to be the expected product.

Example 4—Synthesis of 4-(anthracen-9-yl)-2,3,5,6-tetrafluoropyridine (2). Lithiated anthracene (generated from 1.521 g, 5.915 mmol of 9-bromoanthracene) in diethyl ether (30 mL, 0.1972 M) at −78° C. was added dropwise to perfluoropyridine (1.009 g, 5.968 mmol) dissolved in diethyl ether (15 mL) at −78° C. over a period of 10 min. Upon initial addition of the lithiated anthracene, the reaction mixture turned orange. The reaction mixture was allowed to warm to room temperature during which time the reaction mixture turned a light brown. After 2 h, the reaction was quenched by the addition of methanol (5 mL) followed by the addition of aqueous ammonium chloride. The top ether layer was extracted, dried over magnesium sulfate, and then concentrated under reduced pressure to afford a red viscous oil. The crude product was passed through a silica gel flash column using hexanes/ethyl acetate (3:1, v/v) as the eluent. The collected fractions were dried to give the desired product as a light yellow solid. The synthesis product was analyzed by nuclear magnetic resonance (NMR) spectroscopy, and high-resolution mass spectrometry (HRMS) techniques and found to be the expected product.

Example 5—Synthesis of 2-(anthracen-9-yl)-3,5-difluoro-4,6-bis(4-(phenylethynyl)phenyl)pyridine (2a). Lithiated diphenylacetylene (generated from 0.4289 g, 1.668 mmol of 1-bromo-4-(phenylethynyl)benzene) in diethyl ether (30 mL, 0.0556 M) at −78° C. was added dropwise to 4-(anthracen-9-yl)-2,3,5,6-tetrafluoropyridine (2) (0.2730 g, 0.8341 mmol) dissolved in diethyl ether (15 mL) at −78° C. over a period of 10 min. Upon initial addition of lithiated diphenylacetylene, the reaction mixture turned a deep red/purple. The reaction mixture was allowed to warm to room temperature during which time the reaction mixture turned a bright yellow. After 2 h, the reaction was quenched, first by the addition of methanol (5 mL), followed by the addition of aqueous ammonium chloride. The top ether layer was extracted, dried over magnesium sulfate, and then concentrated under reduced pressure to give a red viscous oil. The crude product was passed through a silica gel flash column using hexanes/ethyl acetate (3:1, v/v) as the eluent. The collected fractions were vacuum dried to give the desired product as a light orange solid. The synthesis product was analyzed by nuclear magnetic resonance (NMR) spectroscopy, and high-resolution mass spectrometry (HRMS) techniques and found to be the expected product.

Example 6—The monomers of Examples 2 and 5 are each processed into polymers by curing the monomers at a temperature range of 300° C. to 450° C. under a nitrogen atmosphere at a heating rate of 5° C./min using a TA DSC Q20 utilizing aluminum pans. Each polymer is then tested in accordance with the Char Percentage test method of the present specification. The following char percentages are obtained for each polymer, 50% for the polymer derived from example 2 and 81% from the polymer derived from example 5.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A monomer having the following formula:

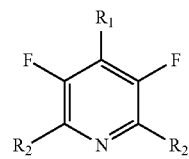

wherein
a) $R_1$ is anthracene or diphenylacetylene; and
b) each $R_2$ is diphenylacetylene.

2. A polymer network comprising a monomer having the following formula:

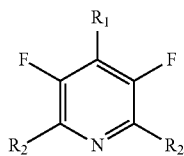

wherein
  a) $R_1$ is anthracene or diphenylacetylene; and
  b) each $R_2$ is diphenylacetylene.

3. The polymer network of claim 2, said polymer network being a homopolymer network.

4. The polymer network of claim 3, said polymer network being a homopolymer network having a char yield of at least 50%.

5. The polymer network of claim 4, said polymer network being a homopolymer network having a char yield of 50% to about 85%.

6. An article comprising a polymer network comprising a monomer having the following formula:

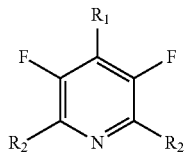

wherein
  a) $R_1$ is anthracene or diphenylacetylene; and
  b) each $R_2$ is diphenylacetylene;
said article being a protective high temperature coating and/or sealant for aerospace vehicles, a protective high temperature coating and/or sealant for motor vehicles, and/or a protective insulating coating for electrical systems and wiring.

7. An article comprising a polymer network comprising a monomer having the following formula:

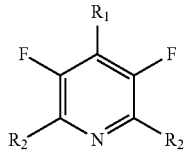

wherein
  a) $R_1$ is anthracene or diphenylacetylene; and
  b) each $R_2$ is diphenylacetylene;
said article being an aerospace vehicle, a motor vehicle or an injection molded and/or 3D printed consumer good.

8. A process of making the monomer of claim 1, said process comprising:
  a) lithiating in a solvent, at a temperature of minus 20° C. to minus 100° C. diphenylacetylene to form lithiated diphenylacetylene;
  b) maintaining the lithation temperature of said lithiated diphenylacetylene and combining said lithiated diphenylacetylene with perfluoropyridine to form a lithiated diphenylacetylene and perfluoropyridine mixture;
  c) allowing said mixture of lithiated diphenylacetylene and perfluoropyridine to react for about one hour to about three hours, said mixture of lithiated diphenylacetylene and perfluoropyridine forming a triacetylic monomer and optional impurities;
  d) quenching said reaction;
  e) scavenging unreacted reactants and/or said optional impurities from said triacetylic monomer by forming a mixture that comprises an organic layer and a aqueous layer, said organic layer comprising the triacetylic monomer and said aqueous layer comprising said unreacted reactants and/or optional impurities;
  f) removing said aqueous layer from said mixture that comprises an organic layer and an aqueous layer;
  g) removing moisture from said organic layer;
  h) filtering off said magnesium sulfate from said organic layer;
  i) removing said solvent from said organic layer.

9. The process according to claim 8, said process comprising:
  a) lithiating in a solvent, at a temperature of minus 40° C. to minus 78° C., diphenylacetylene to form lithiated diphenylacetylene;
  b) maintaining the lithation temperature of said lithiated diphenylacetylene and combining said lithiated diphenylacetylene with perfluoropyridine to form a lithiated diphenylacetylene and perfluoropyridine mixture;
  c) allowing said mixture of lithiated diphenylacetylene and perfluoropyridine to react for about two hours to about two and one half hours, said mixture of lithiated diphenylacetylene and perfluoropyridine forming a triacetylic monomer and optional impurities;
  d) quenching said reaction by the addition of methanol to said triacetylic monomer and optional impurities;
  e) scavenging unreacted reactants and/or said optional impurities from said triacetylic monomer by the addition of any aqueous solution of ammonium chloride to said triacetylic monomer;
  f) removing, by using a separatory funnel, said aqueous layer from said mixture that comprises an organic layer and an aqueous layer;
  g) removing moisture from said organic layer by adding magnesium sulfate to said organic layer;
  h) filtering off said magnesium sulfate from said organic layer;
  i) removing said solvent and said methanol from said organic layer under reduced pressure.

10. The process according to claim 9, said process comprising:
  a) lithiating in a solvent, at a temperature of minus 60° C. to minus 78° C., diphenylacetylene to form lithiated diphenylacetylene;
  b) maintaining the lithation temperature of said lithiated diphenylacetylene and combining said lithiated diphenylacetylene with perfluoropyridine to form a lithiated diphenylacetylene and perfluoropyridine mixture;
  c) allowing said mixture of lithiated diphenylacetylene and perfluoropyridine to react for about two hours to about two and one half hours, said mixture of lithiated diphenylacetylene and perfluoropyridine forming a triacetylic monomer and optional impurities;
  d) quenching said reaction by the addition of methanol to said triacetylic monomer and optional impurities to form a pH neutral triacetylic monomer;
  e) scavenging unreacted reactants and/or said optional impurities from said pH neutral triacetylic monomer by the addition of any aqueous solution of ammonium chloride to said pH neutral triacetylic monomer;
f) removing, by using a separatory funnel, said aqueous layer from said mixture that comprises an organic layer and an aqueous layer;
g) removing moisture from said organic layer by adding magnesium sulfate to said organic layer;
h) filtering off said magnesium sulfate from said organic layer;
i) removing said solvent and said methanol from said organic layer via vacuum distillation.

11. The process of claim 10, said process comprising:
a) lithiating in diethylether at a temperature of minus 60° C. to minus 78° C. diphenylacetylene to form lithiated diphenylacetylene;
b) maintaining the lithation temperature of said lithiated diphenylacetylene and combining said lithiated diphenylacetylene with perfluoropyridine to form a lithiated diphenylacetylene and perfluoropyridine mixture;
c) allowing said mixture of lithiated diphenylacetylene and perfluoropyridine to react for about two hours to about two and one half hours, said mixture of lithiated diphenylacetylene and perfluoropyridine forming a triacetylic monomer and optional impurities;
d) quenching said reaction by the addition of methanol to said triacetylic monomer and optional impurities to form a pH neutral triacetylic monomer;
e) scavenging unreacted reactants and/or said optional impurities from said pH neutral triacetylic monomer by the addition of any aqueous solution of ammonium chloride to said pH neutral triacetylic monomer;
f) removing, by using a separatory funnel, said aqueous layer from said mixture that comprises an organic layer and an aqueous layer;
g) removing moisture from said organic layer by adding magnesium sulfate to said organic layer;
h) filtering off said magnesium sulfate from said organic layer;
i) removing said diethylether and said methanol from said organic layer via vacuum distillation.

12. A process of making the monomer of claim 1, said process comprising:
a) lithiating in a solvent, at a temperature of minus 20° C. to minus 100° C., diphenylacetylene to form lithiated diphenylacetylene and lithiating, in a solvent, a monoanthracene at a temperature of minus 20° C. to minus 100° C., to form lithiated monoanthracene;
b) maintaining the lithation temperature of said lithiated diphenylacetylene and lithiated monoanthracene;
c) combining said lithiated monoanthracene with perfluoropyridine to form a lithiated monoanthracene and perfluoropyridine mixture;
d) allowing said mixture of lithiated monoanthracene and perfluoropyridine to react for about one hour to about three hours to form a monoanthracene perfluoropyridine;
e) combining said monoanthracene perfluoropyridine with said lithiated diphenylacetylene to form a lithiated diphenylacetylene and monoanthracene perfluoropyridine mixture;
f) allowing said mixture of lithiated diphenylacetylene and monoanthracene perfluoropyridine mixture to react for about one hour to about three hours, said mixture of lithiated diphenylacetylene and perfluoropyridine forming a bisacetylic monomer and optional impurities;
g) quenching said reaction;

h) scavenging unreacted reactants and/or said optional impurities from said bisacetylic monomer by forming a mixture that comprises an organic layer and a aqueous layer, said organic layer comprising the bisacetylic monomer and said aqueous layer comprising said unreacted reactants and/or optional impurities;
i) removing said aqueous layer from said mixture that comprises an organic layer and an aqueous layer;
j) removing moisture from said organic layer;
k) filtering off said magnesium sulfate from said organic layer;
l) removing said solvent from said organic layer.

13. The process of claim 12, said process comprising:
a) lithiating in a solvent, at a temperature of minus 40° C. to minus 78° C., diphenylacetylene to form lithiated diphenylacetylene and lithiating, in a solvent, a monoanthracene at a temperature of minus 40° C. to minus 78° C., to form lithiated monoanthracene;
b) maintaining the lithation temperature of said lithiated diphenylacetylene and lithiated monoanthracene;
c) combining said lithiated monoanthracene with perfluoropyridine to form a lithiated monoanthracene and perfluoropyridine mixture;
d) allowing said mixture of lithiated monoanthracene and perfluoropyridine to react for about two hours to about two and one half hours;
e) combining said monoanthracene perfluoropyridine with said lithiated diphenylacetylene to form a lithiated diphenylacetylene and monoanthracene perfluoropyridine mixture;
f) allowing said mixture of lithiated diphenylacetylene and monoanthracene perfluoropyridine mixture to react for about two hours to about two and one half hours, said mixture of lithiated diphenylacetylene and perfluoropyridine forming a bisacetylic monomer and optional impurities;
g) quenching said reaction by the addition of methanol to said bisacetylic monomer and optional impurities;
h) scavenging unreacted reactants and/or said optional impurities from said bisacetylic monomer by forming a mixture that comprises an organic layer and a aqueous layer, said organic layer comprising the bisacetylic monomer and said aqueous layer comprising said unreacted reactants and/or optional impurities, said scavenging comprising the addition of any aqueous solution of ammonium chloride to said bisacetylic monomer;
i) removing, by using a separatory funnel, said aqueous layer from said mixture that comprises an organic layer and an aqueous layer;
j) removing moisture from said organic layer, by adding magnesium sulfate to said organic layer;
k) filtering off said magnesium sulfate from said organic layer;
l) removing, under reduced pressure, said solvents and methanol from said organic layer.

14. The process of claim 13, said process comprising:
a) lithiating in a solvent, at a temperature of minus 60° C. to minus 78° C., diphenylacetylene to form lithiated diphenylacetylene and lithiating, in a solvent, a monoanthracene at a temperature of minus 60° C. to minus 78° C. to form lithiated monoanthracene;
b) maintaining the lithation temperature of said lithiated diphenylacetylene and lithiated monoanthracene;
c) combining said lithiated monoanthracene with perfluoropyridine to form a lithiated monoanthracene and perfluoropyridine mixture;

d) allowing said mixture of lithiated monoanthracene and perfluoropyridine to react for about two hours to about two and one half hours;
e) combining said monoanthracene perfluoropyridine with said lithiated diphenylacetylene to form a lithiated diphenylacetylene and monoanthracene perfluoropyridine mixture;
f) allowing said mixture of lithiated diphenylacetylene and monoanthracene perfluoropyridine mixture to react for about two hours to about two and one half hours, said mixture of lithiated diphenylacetylene and perfluoropyridine forming a bisacetylic monomer and optional impurities;
g) quenching said reaction by the addition of methanol to said bisacetylic monomer and optional impurities and forming a pH neutral bisacetylic monomer;
h) scavenging unreacted reactants and/or said optional impurities from said pH neutral bisacetylic monomer by forming a mixture that comprises an organic layer and a aqueous layer, said organic layer comprising the pH neutral bisacetylic monomer and said aqueous layer comprising said unreacted reactants and/or optional impurities;
i) removing, by using a separatory funnel, said aqueous layer from said mixture that comprises an organic layer and an aqueous layer;
j) removing moisture from said organic layer by adding magnesium sulfate to said organic layer;
k) filtering off said magnesium sulfate from said organic layer;
l) removing said solvents and said methanol from said organic layer via vacuum distillation.

15. The process of claim 14, said process comprising:
a) lithiating in diethylether, at a temperature of minus 60° C. to minus 78° C., diphenylacetylene to form lithiated diphenylacetylene and lithiating, in diethylether, a monoanthracene at a temperature of minus 60° C. to minus 78° C. to form lithiated monoanthracene;
b) maintaining the lithation temperature of said lithiated diphenylacetylene and lithiated monoanthracene;
c) combining said lithiated monoanthracene with perfluoropyridine to form a lithiated monoanthracene and perfluoropyridine mixture;
d) allowing said mixture of lithiated monoanthracene and perfluoropyridine to react for about two hours to about two and one half hours;
e) combining said monoanthracene perfluoropyridine with said lithiated diphenylacetylene to form a lithiated diphenylacetylene and monoanthracene perfluoropyridine mixture;
f) allowing said mixture of lithiated diphenylacetylene and monoanthracene perfluoropyridine mixture to react for about two hours to about two and one half hours, said mixture of lithiated diphenylacetylene and perfluoropyridine forming a bisacetylic monomer and optional impurities;
g) quenching said reaction by the addition of methanol to said bisacetylic monomer and optional impurities to form a pH neutral bisacetylic monomer;
h) scavenging by the addition of any aqueous solution of ammonium chloride to said pH neutral bisacetylic monomer unreacted reactants and/or said optional impurities from said pH neutral bisacetylic monomer by forming a mixture that comprises an organic layer and a aqueous layer, said organic layer comprising the pH neutral bisacetylic monomer and said aqueous layer comprising said unreacted reactants and/or optional impurities;
i) removing, by using a separatory funnel, said aqueous layer from said mixture that comprises an organic layer and an aqueous layer;
j) removing moisture from said organic layer by adding magnesium sulfate to said organic layer;
k) filtering off said magnesium sulfate from said organic layer;
l) removing said diethylether and said methanol from said organic layer via vacuum distillation.

16. The process of making the polymer network of claim 2 said process comprising the steps of curing a monomer having the following formula:

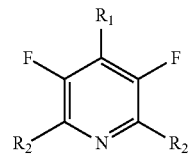

wherein
a) $R_1$ is anthracene or diphenylacetylene; and
b) each $R_2$ is diphenylacetylene;
at a temperature range of 300° C. to 450° C. under a nitrogen atmosphere at a heating rate of 5° C./min.

17. The process of claim 16 comprising curing a monomer mixture comprising a monomer having the following formula:

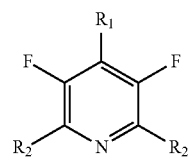

wherein
a) $R_1$ is anthracene or diphenylacetylene; and
b) each $R_2$ is diphenylacetylene;
and one or more additional monomers at a temperature range of 300° C. to 450° C. under a nitrogen atmosphere at a heating rate of 5° C./min.

18. The process of claim 17 wherein said one or more additional monomers is selected from the group consisting of trialkynyl cyanurates, trialkynyl isocyanurates, benzocyclobutanes, bis-ortho-diynyl arenes (BODA), bis-phenylethynyl polyhedral oligomeric silsesquioxanes and mixtures thereof.

19. The process of claim 18 wherein said one or more additional monomers is selected from the group consisting of trialkynyl isocyanurates benzocyclobutanes, bis-ortho-diynyl arenes (BODA), bis-phenylethynyl polyhedral oligomeric silsesquioxanes and mixtures thereof.

20. The process of claim 19 wherein said one or more additional monomers is selected from the group consisting of benzocyclobutanes, bis-ortho-diynyl arenes (BODA), bis-phenylethynyl polyhedral oligomeric silsesquioxanes and mixtures thereof.

21. The process of claim 20 wherein said one or more additional monomers is selected from the group consisting of bis-ortho-diynyl arenes (BODA), bis-phenylethynyl polyhedral oligomeric silsesquioxanes and mixtures thereof.

22. The process of claim 21 wherein said one or more additional monomers is selected form the group consisting of bis-phenylethynyl polyhedral oligomeric silsesquioxanes and mixtures thereof.

* * * * *